(12) United States Patent
Viker et al.

(10) Patent No.: US 11,006,962 B2
(45) Date of Patent: **\*May 18, 2021**

(54) SYSTEMS, TOOLS, AND METHODS FOR CONNECTING TO TISSUE

(71) Applicant: Boston Scientific Scimed, Inc., Maple Grove, MN (US)

(72) Inventors: Thomas O. Viker, Arden Hills, MN (US); Chaouki A. Khamis, Los Gatos, CA (US); Micah D. Thorson, North Branch, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 511 days.

This patent is subject to a terminal disclaimer.

(21) Appl. No.: 15/583,541

(22) Filed: May 1, 2017

(65) Prior Publication Data

US 2017/0231637 A1 Aug. 17, 2017

Related U.S. Application Data

(63) Continuation of application No. 13/832,319, filed on Mar. 15, 2013, now Pat. No. 9,649,114.

(Continued)

(51) Int. Cl.
*A61B 17/12* (2006.01)
*A61B 17/42* (2006.01)
(Continued)

(52) U.S. Cl.
CPC ...... *A61B 17/12009* (2013.01); *A61B 17/064* (2013.01); *A61B 17/068* (2013.01);
(Continued)

(58) Field of Classification Search
CPC .. A61B 17/064–2017/0688; A61B 17/08–105; A61B 17/12–1285;
(Continued)

(56) References Cited

U.S. PATENT DOCUMENTS 2,738,790 A 3/1956 Todt, Sr. et al.
3,875,648 A * 4/1975 Bone ......................... B65C 5/00
29/417

(Continued)

FOREIGN PATENT DOCUMENTS

AU 2013293171 A1 2/2015
CA 2879820 A1 1/2014

(Continued)

OTHER PUBLICATIONS

Extended European Search Report for EP Application No. 13823116.2, dated Aug. 29, 2016, 10 pages.

(Continued)

*Primary Examiner* — Tan-Uyen T Ho
*Assistant Examiner* — Charles M Wei
(74) *Attorney, Agent, or Firm* — Brake Hughes Bellermann LLP

(57) ABSTRACT

Described are various embodiments of surgical procedure systems, devices, tools, and methods, useful for placing a soft tissue anchor at anatomical tissue; these may be useful for general surgical procedures, veterinary procedures, plastic surgery, and for treating pelvic conditions such as vaginal prolapse, incontinence, and other conditions caused by muscle and ligament weakness, the devices and tools being useful for accessing a posterior region of pelvic anatomy, and related methods.

20 Claims, 10 Drawing Sheets

Related U.S. Application Data

(60) Provisional application No. 61/675,050, filed on Jul. 24, 2012.

(51) Int. Cl.
*A61B 17/064* (2006.01)
*A61B 17/068* (2006.01)
*A61B 17/34* (2006.01)
*A61B 17/00* (2006.01)
*A61B 17/04* (2006.01)

(52) U.S. Cl.
CPC .......... *A61B 17/3468* (2013.01); *A61B 17/42* (2013.01); *A61B 17/12013* (2013.01); *A61B 2017/00805* (2013.01); *A61B 2017/0419* (2013.01); *A61B 2017/0464* (2013.01); *A61B 2017/0472* (2013.01); *A61B 2017/0647* (2013.01)

(58) Field of Classification Search
CPC .... A61B 2017/0409; A61B 2017/0417; A61B 2017/0419; A61B 2017/0416; A61B 2017/07278
See application file for complete search history.

(56) References Cited

U.S. PATENT DOCUMENTS

| | | | |
|---|---|---|---|
| 3,948,128 A * | 4/1976 | Russell | B65C 7/006 83/110 |
| 4,471,781 A * | 9/1984 | Di Giovanni | A61B 17/0491 606/145 |
| 4,548,202 A | 10/1985 | Duncan | |
| 4,586,502 A * | 5/1986 | Bedi | A61B 17/04 606/144 |
| 4,621,639 A * | 11/1986 | Transue | A61B 17/04 606/215 |
| 4,696,300 A * | 9/1987 | Anderson | A61B 17/04 273/DIG. 5 |
| 4,724,840 A * | 2/1988 | McVay | A61B 17/0491 606/215 |
| 4,848,637 A * | 7/1989 | Pruitt | A61B 17/072 227/19 |
| 4,873,976 A | 10/1989 | Schreiber | |
| 4,932,962 A | 6/1990 | Yoon et al. | |
| 5,020,713 A | 6/1991 | Kunreuther | |
| 5,085,661 A | 2/1992 | Moss | |
| 5,112,344 A | 5/1992 | Petros | |
| 5,203,864 A | 4/1993 | Phillips | |
| 5,209,756 A | 5/1993 | Seedhom et al. | |
| 5,381,943 A * | 1/1995 | Allen | A61B 17/0682 227/177.1 |
| RE34,857 E * | 2/1995 | Kunreuther | B65C 7/005 227/67 |
| 5,518,162 A | 5/1996 | Deschenes et al. | |
| 5,562,689 A | 10/1996 | Green et al. | |
| 5,575,799 A * | 11/1996 | Bolanos | A61B 17/0684 227/175.1 |
| 5,611,515 A | 3/1997 | Benderev et al. | |
| 5,842,478 A | 12/1998 | Benderev et al. | |
| 5,860,425 A | 1/1999 | Benderev et al. | |
| 5,899,909 A | 5/1999 | Claren et al. | |
| 5,972,000 A | 10/1999 | Beyar et al. | |
| 5,997,552 A * | 12/1999 | Person | A61B 17/064 606/139 |
| 6,039,686 A | 3/2000 | Kovac | |
| 6,042,534 A | 3/2000 | Gellman et al. | |
| 6,048,351 A | 4/2000 | Gordon et al. | |
| 6,071,290 A | 6/2000 | Compton | |
| 6,099,551 A | 8/2000 | Gabbay | |
| 6,099,552 A | 8/2000 | Adams | |
| 6,110,101 A | 8/2000 | Tihon et al. | |
| 6,267,286 B1 * | 7/2001 | Deschenes | A41H 37/008 227/67 |
| 6,494,906 B1 | 12/2002 | Owens | |
| 6,612,977 B2 | 9/2003 | Staskin et al. | |
| 6,648,921 B2 | 11/2003 | Anderson et al. | |
| 6,666,872 B2 | 12/2003 | Barreiro et al. | |
| 6,691,711 B2 | 2/2004 | Raz et al. | |
| 7,025,063 B2 | 4/2006 | Snitkin et al. | |
| 7,160,314 B2 * | 1/2007 | Sgro | A61B 17/064 606/139 |
| 7,303,525 B2 | 12/2007 | Watschke et al. | |
| 7,347,812 B2 | 3/2008 | Mellier | |
| 7,351,197 B2 | 4/2008 | Montpetit et al. | |
| 7,407,480 B2 | 8/2008 | Staskin et al. | |
| 7,485,124 B2 * | 2/2009 | Kuhns | A61B 17/064 606/151 |
| 7,500,945 B2 | 3/2009 | Cox et al. | |
| 7,572,266 B2 * | 8/2009 | Young | A61B 17/1285 606/143 |
| 7,819,897 B2 * | 10/2010 | Sgro | A61B 17/064 606/139 |
| 9,649,114 B2 * | 5/2017 | Viker | A61B 17/12009 |
| 2001/0010005 A1 * | 7/2001 | Kammerer | A61B 17/064 606/151 |
| 2002/0028980 A1 | 3/2002 | Thierfelder et al. | |
| 2002/0147382 A1 | 10/2002 | Neisz et al. | |
| 2002/0151762 A1 | 10/2002 | Rocheleau et al. | |
| 2004/0138683 A1 * | 7/2004 | Shelton | A61B 17/0401 606/151 |
| 2005/0187567 A1 * | 8/2005 | Baker | A61B 17/0401 606/151 |
| 2005/0288708 A1 * | 12/2005 | Kammerer | A61B 17/0644 606/221 |
| 2006/0122636 A1 * | 6/2006 | Bailly | A61B 17/0401 606/142 |
| 2007/0005080 A1 * | 1/2007 | Wolniewicz | A61B 17/0401 606/142 |
| 2008/0065120 A1 * | 3/2008 | Zannis | A61B 17/0401 606/144 |
| 2009/0093824 A1 * | 4/2009 | Hasan | A61B 17/0401 606/139 |
| 2010/0010511 A1 | 1/2010 | Harris et al. | |
| 2010/0174134 A1 | 7/2010 | Anderson et al. | |
| 2010/0179575 A1 * | 7/2010 | Von Pechmann | A61B 17/0401 606/151 |
| 2010/0256442 A1 | 10/2010 | Ogdahl et al. | |
| 2010/0298630 A1 | 11/2010 | Wignall | |
| 2011/0034759 A1 | 2/2011 | Ogdahl et al. | |
| 2012/0022318 A1 | 1/2012 | Thierfelder et al. | |
| 2013/0006061 A1 | 1/2013 | Alexander et al. | |
| 2013/0035543 A1 | 2/2013 | Fischer et al. | |
| 2013/0035555 A1 | 2/2013 | Alexander et al. | |
| 2014/0135771 A1 * | 5/2014 | Bhatnagar | A61B 17/064 606/75 |

FOREIGN PATENT DOCUMENTS

| | | |
|---|---|---|
| EP | 0508452 A1 | 10/1992 |
| EP | 2884903 A1 | 6/2015 |
| WO | 1995/019914 A1 | 7/1995 |
| WO | 1997/047244 A1 | 12/1997 |
| WO | 2000/040158 A2 | 7/2000 |
| WO | 2007/097994 A2 | 8/2007 |
| WO | 2007/149348 A2 | 12/2007 |
| WO | 2008/057261 A2 | 5/2008 |
| WO | 2010/093421 A2 | 8/2010 |
| WO | 2011/028564 A2 | 3/2011 |
| WO | 2011/063412 A2 | 5/2011 |
| WO | 2011/072148 A1 | 6/2011 |
| WO | 2011/082350 A1 | 7/2011 |
| WO | 2014/018473 A1 | 1/2014 |

OTHER PUBLICATIONS

International Search report and Written Opinion for PCT Patent Application No. PCT/US2013/051563, dated Nov. 20, 2013, 9 pages.

(56) References Cited

OTHER PUBLICATIONS

International Preliminary Report on Patentability for PCT Patent Application No. PCT/US2013/051563, dated Feb. 5, 2015, 8 pages.
Extended European Search Report for European Application No. 19161745.5, dated Oct. 2, 2019, 11 pages.

\* cited by examiner

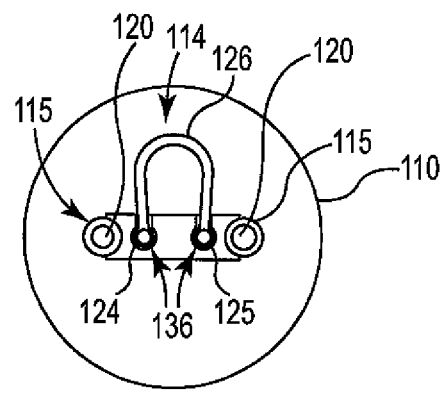
Fig. 1C
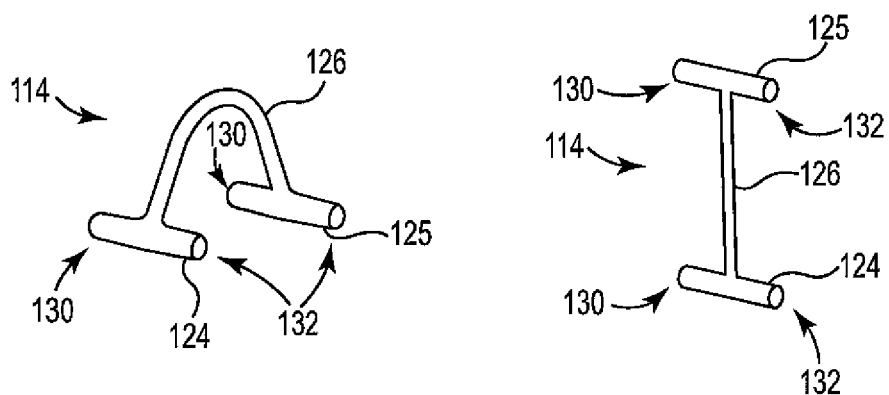
Fig. 2A
Fig. 2B

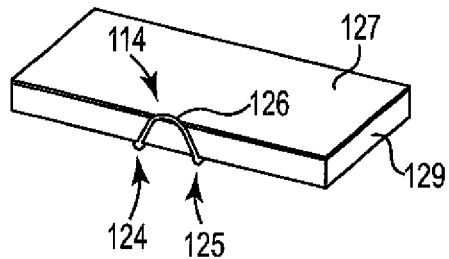 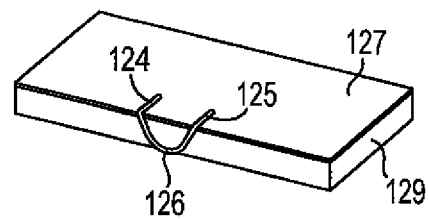
Fig. 3A Fig. 3B
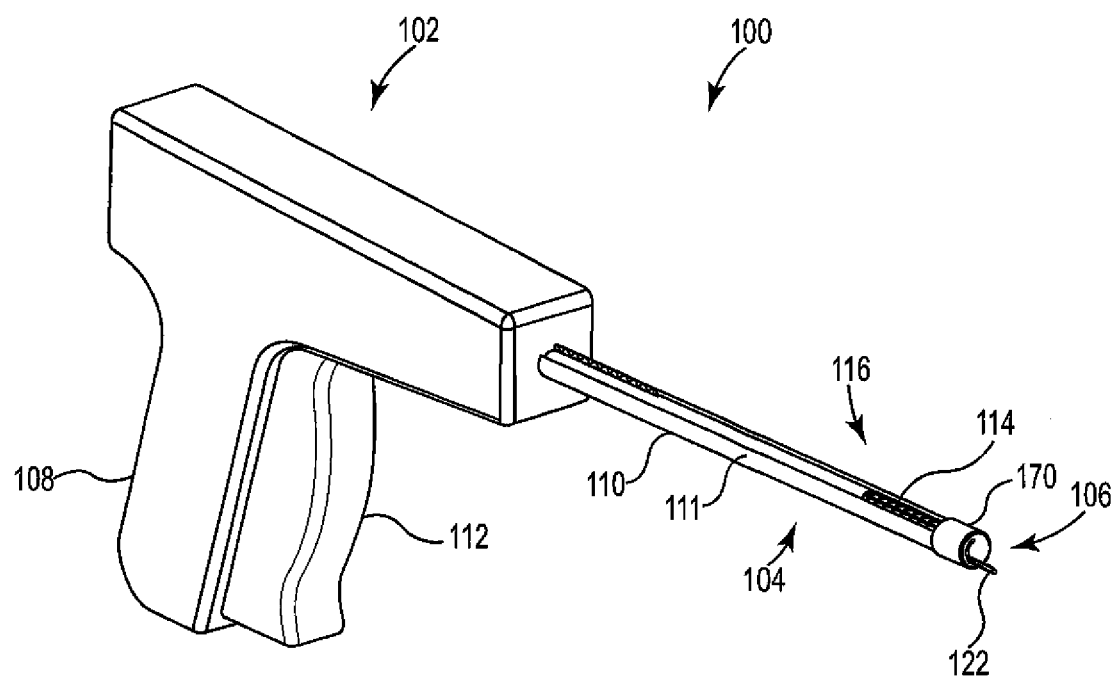
Fig. 4

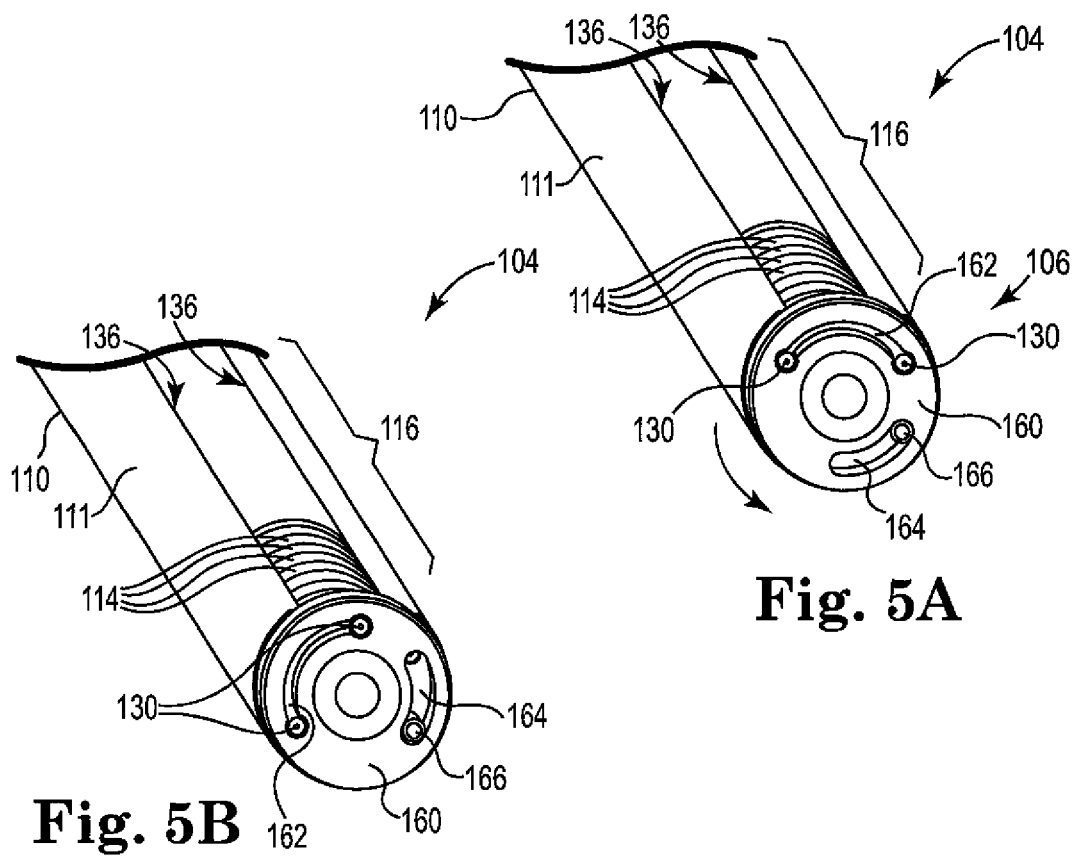
Fig. 5A
Fig. 5B
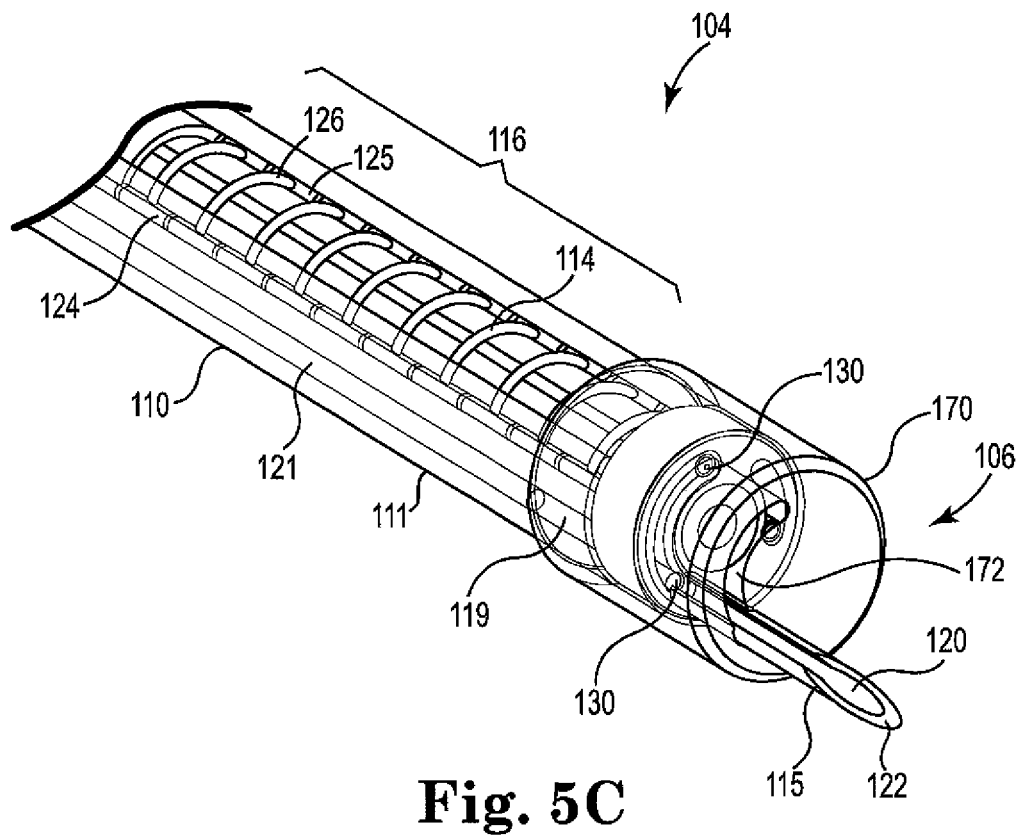
Fig. 5C

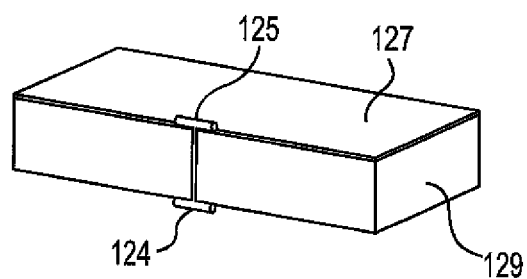
Fig. 6
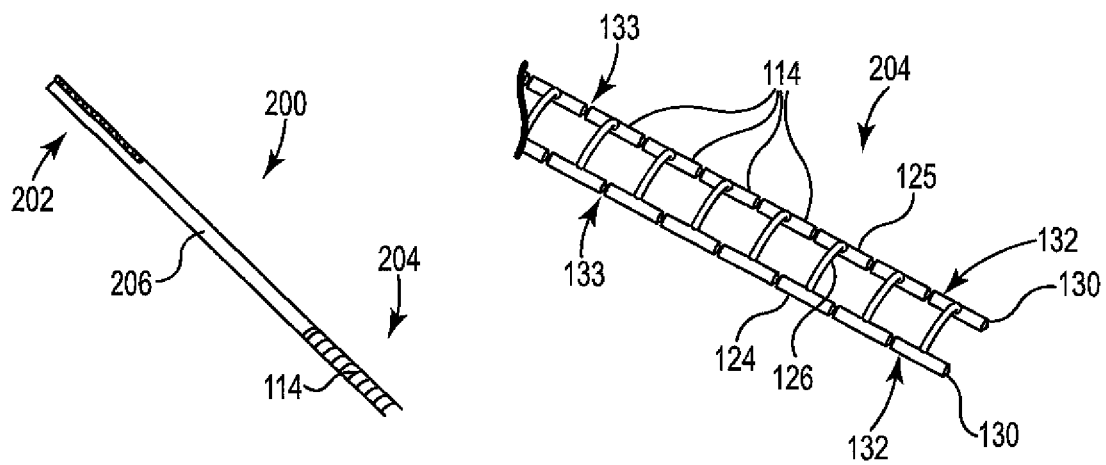
Fig. 7A  Fig. 7B

SYSTEMS, TOOLS, AND METHODS FOR CONNECTING TO TISSUE

CROSS-REFERENCE TO RELATED APPLICATIONS

This application is a Continuation of, and claims priority to, U.S. patent application Ser. No. 13/832,319, filed on Mar. 15, 2013, entitled "SYSTEMS, TOOLS, AND METHODS FOR CONNECTING TO TISSUE", which claims priority to U.S. patent application Ser. No. 61/1675,050, filed on Jul. 24, 2012, entitled "SYSTEMS, IMPLANTS, TOOLS, AND METHODS FOR TREATMENTS OF PELVIC CONDITIONS", the disclosures of which are incorporated by reference herein in their entirety.

FIELD OF THE INVENTION

The invention relates to systems, tools, and related methods for surgically treating a condition by making a connection to tissue, e.g., by connecting an implant to tissue, or by connecting tissue to another tissue, for example to treat a pelvic condition, for use in general surgery, or for use in particular surgical specialties such as plastic surgery. For pelvic applications, a pelvic condition may be a condition treated by placement of an implant in a male or female patient, including but not limited to a condition of levator tissue; incontinence (urinary or fecal); hernia repair, and prolapse conditions, for example treatment of vaginal and vaginal vault prolapse; a method can be performed by a transvaginal, abdominal, or laparoscopic procedure.

BACKGROUND

The fields of medicine and surgical medicine involve methods and structures useful for connecting tissue, and for connecting surgical items such as implants to tissue. Medical and surgical sutures are ubiquitous for these purposes. These can take the form of a natural or synthetic thread or other fibrous or filamentary structure that is passed through tissue, optionally passed through or around an implant or other surgical item, and then tied off to secure the tissue and tissue, or tissue and surgical item, in place.

The use of sutures is not perfect or even highly suitable for all surgical and medical procedures. For example, sutures are best tied by a surgeon or other medical professional manually, with assistance of tools such as a suture passing needle, needle driver, knot pusher, forceps, and other surgical tools. This works well when the surgeon or medical professional has open access to the site of the suture, but less well when the suture must be tied in a constrained location or through tight access to the location. For those situations, a surgeon may experience difficulty placing the suture at its most effective or desired location, and tying the suture to best secure tissue to tissue or tissue to an implant.

Potential replacements for sutures have long been the subject of product research. Over time, countless examples of non-suture suture-replacement devices, related delivery tools, and related methods, have been developed and tried in efforts to replace the ubiquitous suture with an easier to use device. Examples include surgical staples and biologic adhesives useful to hold tissue to tissue or tissue to an implant, and soft tissue anchors useful to secure surgical implants directly at patient tissue. Many of these have been used in particular applications that require placement of a suture at a difficult-to-reach surgical site or through a tight or deep surgical access path. Examples of these types of applications include surgical procedures that are performed laparoscopically and surgical procedures that are performed transvaginally in a female patient or through a comparable medial or perinea! tissue surgical access incision in a male patient. Many of these procedures are performed for treating a pelvic health condition such as prolapse or incontinence.

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), conditions of the pelvic floor such as levator avulsion or prolapse, and hernias.

Incontinence includes all various forms of anal (fecal) and urinary incontinence in a male or female. Vaginal prolapse in a female patient can be in the form of a cystocele, rectocele, enterocele, or vaginal vault prolapse, some of which can occur in combination with anal or urinary incontinence. In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times. Sacralcolpopexy (SCP) procedures are considered to be especially efficacious methods for treating vaginal vault prolapse. Various methods of placing slings or other implants for treating urinary or fecal continence are commonly used.

Still, there ongoing research and development of new and effective methods of surgically connecting tissue or surgically placing supportive implants for treating pelvic conditions in male and female patients, such as hernias, vaginal prolapse, incontinence, and other conditions affecting pelvic tissue and function. More generally, continuing interest exists for suture replacements in general surgical procedures in both humans and animals (i.e., in veterinary medicine), and in specific surgical specialties (e.g., plastic surgery).

SUMMARY

Devices, systems, methods, and items (fasteners and tools) as described can be useful to connect two pieces of anatomical tissue together, or to connect another item such as a surgical implant, to tissue. Examples of certain devices, systems, and methods as described can be used to treat pelvic conditions such as incontinence (various forms such as fecal incontinence, stress urinary incontinence, urge incontinence, mixed incontinence, etc.), hernia, vaginal prolapse (including various forms such as enterocele, cystocele, rectocele, apical or vault prolapse, uterine descent, etc.), levator muscle conditions (e.g., avulsion) and other conditions caused by muscle and ligament weakness, hysterectomies and the like. In other applications, the devices, systems, and methods may be useful in general surgical procedures, in veterinary medicine (surgical or non-surgical), in plastic surgery, or in any other medical use that involves attaching tissue to tissue, or attaching a medical device such as an implant or similar material to tissue.

Certain described embodiments relate generally to surgical methods and apparatus and, more specifically, to soft tissue anchor delivery devices capable of delivering a soft tissue anchor to pelvic tissue, through a surgical incision. Embodiments of soft tissue anchor delivery device may be capable of supporting, holding, manipulating, advancing and ejecting a soft tissue anchor at a surgical location to secure an implant material to soft tissue or to connect tissue to tissue. Various such embodiments of soft tissue anchor delivery devices can include an elongate shaft having a proximal end and a distal end. A handle can be situated at the proximal end. The proximal end can also include an actuator, such as a trigger, button, lever, or other movement, useful to manipulate one or more distal end functionality operative upon a soft tissue anchor.

The distal end of the elongate shaft may include a magazine or other space to hold one or (preferably) multiple soft tissue anchors, such as a series of soft tissue anchors. The anchor or anchors can be held in the magazine, which can extend along a length of the shaft between the distal end tip and the proximal end.

An aspect of the invention relates to a soft tissue anchor delivery device in combination with a soft tissue anchor. The soft tissue anchor includes a first elongate leg, a second elongate leg, and a tie connecting the first elongate leg to the second elongate leg. The delivery device includes: a proximal end and a distal end, the proximal end having a handle; and a shaft extending from the handle to the distal end. The distal end includes: a magazine and a staging location on a distal side of the magazine. The device also includes an ejector that can be actuated to eject a soft tissue anchor from the staging location.

In another aspect the invention relates to a method of placing a soft tissue anchor at anatomical tissue. The method includes providing a soft tissue anchor having a first elongate leg, a second elongate leg, and a tie connecting the first elongate leg to the second elongate leg. Providing a delivery device that includes: a proximal end and a distal end, the proximal end having a handle; and a shaft extending from the handle to the distal end. The method also includes placing the distal end of the device at a location of anatomical tissue, and ejecting the soft tissue anchor from a distal end of the device to place a portion of the soft tissue anchor in the anatomical tissue.

In another aspect the invention relates to a series of connected soft tissue anchors. The series of anchors includes a first soft tissue anchor having a first leg having a distal end and a proximal end, a second leg having a distal end and a proximal end, and a tie having a first tie end and a second tie end, the first tie end being connecting the a medial location of the first leg and the second tie end being connected to a medial location of the second leg. The series also includes a second soft tissue anchor having a first leg having a distal end and a proximal end, a second leg having a distal end and a proximal end, and a tie having a first tie end and a second tie end, the first tie end being connecting the a medial location of the first leg and the second tie end being connected to a medial location of the second leg. The distal ends of the legs of the first soft tissue anchor are connected to the proximal ends of the legs of the second soft tissue anchor.

BRIEF DESCRIPTION OF THE DRAWINGS

FIGS. 1A, 1B, and 1C shows an example of a delivery device as described.

FIGS. 2A and 2B show examples of soft tissue anchors as described.

FIGS. 3A and 3B show use configurations of an anchor placed in contact with tissue, to secure an implant (or, alternately, another tissue) to the tissue.

FIGS. 4, 5A, 5B, and 5C show an example of a delivery device as described.

FIG. 6 shows a use configuration of an anchor placed in contact with tissue, to secure an implant (or, alternately, another tissue) to the tissue.

FIGS. 7A, 7B, 7C, and 7D show an example of anchors as described, configured in a strip.

DETAILED DESCRIPTION

Figure 1A:
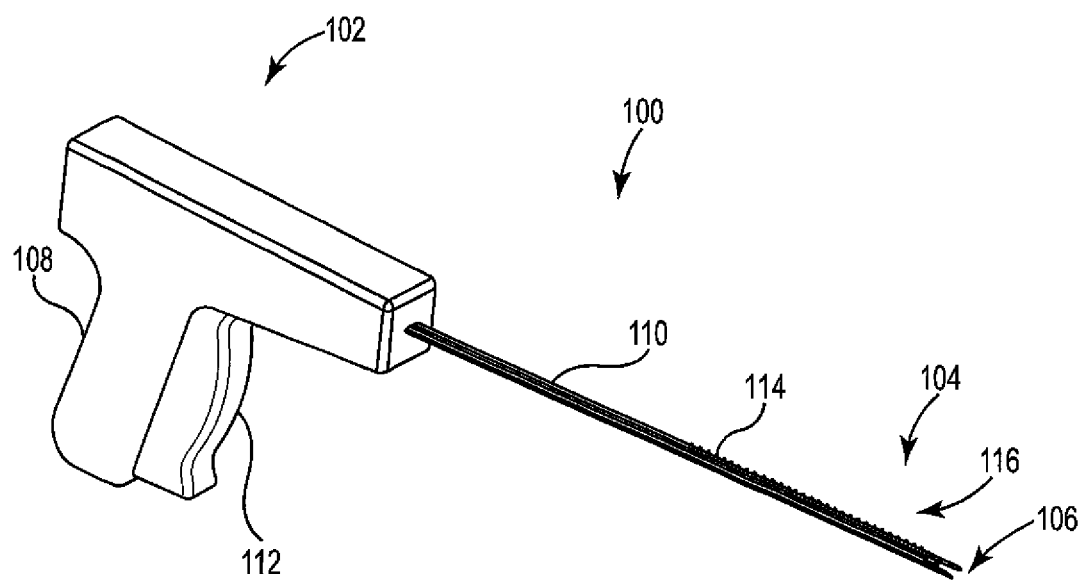

This description relates to the use of tissue fasteners, tissue anchors, or "sutureless" fasteners useful to secure anatomically to a tissue, to either secure an item such as an implant material to the tissue, or to secure another anatomical tissue to the first tissue. Much of the present description relates to methods of using a tissue fastener in certain surgical applications, such as to secure an implant to a pelvic tissue for treating, e.g., hernia, incontinence, prolapse, or the like. This emphasis in the present description of those exemplary applications, of a tissue fastener being used to at a pelvic tissue, is not to be considered as limiting the broader concepts and principles found in the present descriptions. In specific, various and multiple other medical and surgical medical uses of the described tissue fasteners, insertion tools, systems, and methods will be apparent based on the present description, and can include any past, present, or future use or application by which as soft tissue anchor or suture can be secured to anatomical tissue. As other examples, these devices, fasteners, insertion tools, and methods may be useful in general medical and surgical procedures in humans and animals, and may specifically be useful in plastic surgery in humans; in all instances the devices and methods may be useful for connecting tissue to tissue, or for connecting tissue to another item such as a surgical implant.

In the specific application of treatment of pelvic conditions, pelvic floor disorders include hernia, cystocele, rectocele, enterocele, incontinence (e.g., urinary and fecal incontinence), and uterine and vaginal vault prolapse, among others. These disorders typically result from weakness or damage to normal pelvic muscle or support systems. Common etiologies include childbearing, removal of the uterus, connective tissue defects, prolonged heavy physical labor, and postmenopausal atrophy.

Vaginal vault prolapse is often associated with a rectocele, cystocele, or enterocele. It is known to repair vaginal vault prolapse by connecting vaginal tissue to supraspinous ligament by sutures, or to attach vaginal tissue through mesh or fascia to tissue at a region of the sacrum. Many patients suffering from vaginal vault prolapse also require a surgical procedure to correct stress urinary incontinence that is either symptomatic or latent.

A sacral colpopexy is a procedure for providing vaginal vault suspension. It may be performed through an abdominal incision ("open surgery"), a vaginal incision, or laparoscopically, and entails suspension (by use of an implant such as a strip of mesh) of the vaginal cuff (apex) to a region of sacral anatomy such as the sacrum (bone itself), or anterior longitudinal ligament at the sacral promontory. In some SCP procedures that also involve a hysterectomy, an implant can attach to posterior vaginal tissue remaining after removal of the uterus and cervix, and attaches also to supportive tissue at or around the sacrum (i.e., to a component of the sacral anatomy). Alternate procedures attach to a sacrospinous ligament or uterosacral ligament.

Devices, systems, and methods as described herein can be useful for placing a pelvic implant in a sacral colpopexy procedure, but can also be useful in treating other pelvic conditions, such as a hernia, urinary or fecal incontinence in a male or female patient, or defects, injury, or prolapse of levator tissue. Sling procedures for treating urinary incontinence include surgical methods that place a supportive implant such as a sling to stabilize or support the bladder neck or urethra. A variety of different supportive implants and sling procedures are known. Slings and methods can differ based on the type of sling material and anchoring methods used, and placement and technique for placing and supporting the sling, including tissue to be supported. In some cases, a sling is placed under the bladder neck and secured via suspension sutures to a point of attachment (e.g. bone) through an abdominal or vaginal incision. Other techniques place a supportive portion of a sling below a urethra or bladder neck, and support the sling by placement of ends at or through obturator foramen tissue. Examples of sling procedures are disclosed in U.S. Pat. Nos. 5,112,344; 5,611,515; 5,842,478; 5,860,425; 5,899,909; 6,039,686, 6,042,534 and 6,110,101.

As used herein, the terms "anchor" and "fastener" refer non-specifically to any structure that can connect tissue, or that can connect an implant to tissue, e.g., of a pelvic region. The tissue may be soft tissue such as a muscle, fascia, ligament, tendon, or the like (i.e., supportive tissue). The anchor or fastener may be any known or future-developed structure useful to connect to such tissue, including but not limited to an "H"-style or "I"-style plastic soft tissue anchors as shown herein, such as at FIG. 2B and other figures.

Examples of systems, devices, tools, implants, etc., described herein can be useful in medical or surgical instruments, assemblies, implantable supportive implants, systems, and related methods for treating a pelvic condition including prolapse (e.g., any form of vaginal prolapse), urinary incontinence, fecal incontinence, levator defects, etc., in a male or female patient, and hernias. An implant can be implanted in a male or a female to treat a condition such as prolapse, urge incontinence, mixed incontinence, overflow incontinence, functional incontinence, hernia, and the like.

An implant can include a tissue support portion (or "support portion") that can be used to support a urethra (including a bladder neck), bladder, vaginal tissue (e.g., vaginal apex), levator, rectum, sphincter, abdominal muscle, or other pelvic tissue (these tissues referred to generally as "supported tissue"). Supporting a "urethra" refers to supporting tissue that includes the urethra (which can refer to the bladder neck), and that can optionally include tissue adjacent to a urethra such as bulbospongiosus muscle, corpus spongiosum, or both.

An implant can additionally include one or more extension portion (otherwise known as an "end" portion or "arm") attached or attachable to the tissue support portion. Normally, for treating incontinence or for treating vaginal vault prolapse, an implant can include two or four extension portions. Extension portions are elongate pieces of material (e.g., mesh, molded implant material, suture, or biologic material) that extend from the tissue support portion and either are or can be connected to the tissue support portion, and are useful to attach to anatomical features or "supportive tissue" in the pelvic region (e.g., using an anchor or fastener) to thereby provide support for the tissue support portion and the supported tissue. Generally for treating incontinence, two extension portions can extend from opposite ends of a tissue support portion as elongate "ends," "arms," or "extensions," and may attach to supportive tissue in the pelvic region by extending through a tissue path to an internal anchoring point (see, e.g., Applicant's co-pending application having U.S. Publication No. 2010/256442, filed Aug. 8, 2008, by Ogdahl, entitled SURGICAL ARTICLES AND METHODS FOR TREATING PELVIC CONDITIONS, the entirety of which is incorporated herein by reference). Also see U.S. Publication No. 2011/0034759 and International Patent Publication Nos. WO 2010/093421, WO 2011/063412, and WO 2011/072148, the entireties of which are incorporated herein by reference. Soft tissue anchors, systems, and method as described herein can be useful with any of these and similar surgical implants and methods, e.g., by which a soft tissue anchor as described is used to securing an extension portion of an implant at a location to secure the implant to tissue, e.g., at supportive tissue.

In exemplary uses, each extension portion can extend from the location of attachment with the tissue support portion, through pelvic tissue or space, and optionally be attached to supportive tissue within the pelvic region. For certain procedures, the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. Other supportive tissue for different procedures (e.g., prolapse) include a ligament, tendon, or muscle in the pelvic region such as an arcus tendinous, sacrospinous ligament, abdominal muscle (e.g., for hernia repair), or levator muscle, or tissue of a region of a sacrum such as an anterior longitudinal ligament.

An implant may include portions, pieces, or sections that are synthetic or of biologic material (e.g., porcine, cadaveric, etc.). Extension portions may be, e.g., a synthetic mesh such as a polypropylene mesh, a suture, a molded implant material, or the like. The tissue support portion may be synthetic (e.g., a polypropylene mesh or a molded material) or biologic. Examples of implant products that may be similar to those useful according to the present description include those sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Spare®, Bioarc®, Monarc®, MiniArc®, InVance™, and AdVance™ for treating urinary incontinence.

Pelvic implant installation procedures (e.g., SCP procedures) may be performed through an abdominal opening (by open abdominal surgery), laparoscopically (e.g., through a laparoscopic incision in an abdomen), transvaginally in a female patient, or through a medial (perineal) incision in a male patient. According to methods described herein, a soft tissue anchor delivery device can be used to deliver a soft tissue anchor to a surgical site of a pelvic implant installation procedure, to secure an implant material (e.g., an extension portion of an implant) at the surgical site. A soft tissue anchor delivery device can be used in the described methods in a minimally invasive transvaginal SCP procedure, in a laparoscopic SCP procedure, or in an abdominal SCP procedure that involves an open (non-laparoscopic) abdominal incision. In alternate treatments, a soft tissue anchor delivery device can be used in a transvaginal, laparoscopic, or abdominal procedure for treating other conditions such as female vaginal prolapse (cystocele, enterocele, rectocele), male or female urinary or fecal incontinence, a hernia, or a condition of levator tissue (e.g., prolapsed or damaged levator tissue). Examples of methods and implants useful in pelvic procedures, including sacral colpopexy procedures, are described in Assignee's co-pending International Patent Application having International Patent Application No. PCT/US2010/062577, filed Dec. 30, 2010, published as WO 2011/082350; Assignee's co-pending provisional patent application having U.S. Ser. No. 61/515,160, filed Aug. 4, 2011; Assignee's co-pending provisional patent application having U.S. Ser. No. 61/515,685, filed Aug. 5, 2011; Assignee's co-pending application having U.S. Publication No. 2013/0006061, filed Jun. 29, 2012; Assignee's co-pending application having U.S. Publication No. 2013/0035543, filed Aug. 3, 2012; Assignee's co-pending application having U.S. Publication No. 2013/0035555, filed Oct. 4, 2011; and Assignee's co-pending application having U.S. Publication No. 2012/0022318, filed Oct. 4, 2011, the entireties of which are incorporated herein by reference.

According to presently described systems, devices, and methods, a soft tissue anchor delivery device can be useful for accessing and delivering a soft tissue anchor to a surgical location in a male or female pelvic anatomy during a transvaginal (in female patients), perinea} (in a male), laparoscopic, open surgical, or trans-abdominal pelvic procedure, for example to access tissue of the posterior pelvic region such as to perform an SCP procedure, to perform repair of a hernia, or to treat another pelvic condition. The soft tissue anchor will also attach to an implant material, securing the implant material at a location of the soft tissue anchor and adjacent tissue.

The soft tissue anchor can be of a type sometimes referred to herein as a sutureless anchor or a plastic fastener, which is different from fasteners generally referred to as a suture, a knot, or a staple; soft tissue anchors of the type referred to as sutureless anchors or plastic fasteners can be plastic anchors that include two legs and a tie, the two legs being connected by the tie; each of the two legs and the tie is elongate and has a length, and the tie has two ends. A first end of the tie connects to one of the legs, e.g., along a length of the leg, and the second end connects to the other (second) leg, e.g., along a length of the other (second) leg. Exemplary anchors can be in the form of an "H" or "I" but other forms are also useful, such as a form wherein the tie is bent or curved.

The soft tissue anchor can be of any useful dimension. In use, the two ends and the tie work together to engage tissue and an implant to secure the implant at a therapeutic or otherwise desired location of the tissue. In one exemplary use configuration, one leg is placed below tissue, the second leg is placed above tissue, and an implant is held against tissue by the second leg (see FIG. 6). In another exemplary use configuration, one leg is placed below tissue, the second leg is also placed below tissue, and the tie extends between the first leg and the second leg passing out of the tissue and passing through an implant such that the tie engages and holds the implant against the tissue (see FIG. 3A). In still another exemplary use configuration, one leg is placed above tissue, the second leg is also placed above the tissue, and the tie extends between the first leg and the second leg passing below the surface of and through the mass of the tissue such that the tie engages and holds the tissue and the first and second legs hold the implant against the tissue (see FIG. 3B).

The soft tissue anchor can be prepared from any useful material, for example a useful biocompatible polymer, which may either be bioresorbable or non-bioresorbable. As opposed to a staple, which is typically made of metal or other similar material that is permanently deformed during use, the soft tissue anchor can preferably be made of a material that is sufficiently flexible and resilient to not become substantially permanently deformed upon being ejected from a distal end of a soft tissue anchor dispensing device, or upon being otherwise manipulated or handled during uses described herein. Examples of useful materials include flexible plastics such as polyethylene, polypropylene, and other thermoplastic or thermoformable materials, as well other types of biocompatible and optionally bioabsorbable or bioresorbable materials. Exemplary bioabsorbable materials include, e.g., polyglycolic acid (PGA), polylactide (PLA), copolymers of PGA and PLA.

The soft tissue anchor and its constituent legs and tie can be of any dimensions useful to allow use of the soft tissue anchor according to a medical use or a surgical use to connect tissue to tissue or to connect tissue to an implant, such as by a transvaginal, laparoscopic, or open surgical method. The overall size of the soft tissue anchor can be such that the soft tissue anchor can be inserted through a transvaginal, laparoscopic, or open surgical incision. For a laparoscopic incision, the soft tissue anchor must be sufficiently small to be inserted through a laparoscopic cannula and a small incision, as are used in laparoscopic techniques. Preferred soft tissue anchors may be flexible to allow improved ease of placement through a surgical incision or laparoscopic cannula. Specific dimensions of the first and second legs and the tie may also be as required to function in the manner described herein, e.g., to secure a surgical implant to tissue. A leg can have a length that will be sufficient to secure the leg within tissue, if placed in tissue (see FIGS. 3A and 6). Alternately, a leg can have a length that will be sufficient to retain an implant material at a location along the length of the tie, such as to keep the implant material located adjacent to and external to tissue if a first leg of the soft tissue anchor, or a tie of the soft tissue anchor, is placed under the tissue and the second leg (and optionally a first leg) is passed through an implant material (see FIGS. 3B and 6). A tie that connects one leg to the second leg should be of a sufficient length to allow the tie to secure an implant material to tissue with one or two legs of the soft tissue anchor placed within tissue of a patient (see FIGS. 3A and 6), or with both legs above the tissue (see FIG. 3B).

As more specific examples, a leg of a soft tissue anchor can be of a length in a range from about 0.10 to about 1 inch, such as from 0.15 to 0.75 inch. A length of one leg of a soft tissue anchor may be the same as or different from a length of a second leg of the same soft tissue anchor. A length of a tie of a soft tissue anchor can be of a length in a range from about 0.1 to about 1 inch, such as from 0.15 to 0.75 inch. Each of the tie and legs can exhibit a cross section that is preferably solid, and that can be of any form, such as a circular, square, rectangular, triangular, oval, or otherwise shaped cross section. A width dimension of the cross section (e.g., diameter) of each of the legs and tie can be as desired, with examples of a cross-sectional dimension being from about 0.01 to about 0.1 inch, e.g., from 0.015 to 0.08 inch.

Referring to FIG. 2A, tissue fastener 114 includes leg 124, second leg 125, and tie 126. Tie 126 is shown to be biased to include a curve. Each of legs 124 and 125 includes a distal end 130, a proximal end 132, and a length therebetween; ends of tie 126 connect to legs 124 and 125 at a position along a length of each leg, e.g., at a medial location as illustrated. A length of each of legs 124 and 125 can be as described, for example in a range from about 0.2 to about 0.3 inch (other ranges will also be useful, depending on the application); a length of tie 116, between legs 124 and 125, can be as described, for example in a range from about 0.28 to about 0.32 inch (other ranges also being useful for various applications).

A soft tissue anchor delivery device includes a proximal end with a handle, and an elongate shaft for reaching and accessing tissue at a surgical site through a surgical incision. The shaft can have a length to allow access and delivery of a soft tissue anchor to a desired surgical site, when the elongate shaft is placed transabdominally, laparoscopically, or transvaginally, or at an open surgical site, e.g., a length to allow a distal end of the device to reach desired tissue while the shaft of the device extends through an abdominal, laparoscopic, vaginal, or other another surgical incision, and the proximal end and optional handle are located externally to the patient. A proximal end and optional handle of a soft tissue anchor delivery device remain external to the patient during use to allow a surgeon or other user to access and manipulate the proximal end, to thereby place and control the distal end at a surgical site. A soft tissue anchor can be located and held at the distal end, and can be placed as desired at tissue of a surgical site, then ejected into the tissue by manipulation of the proximal end.

Exemplary lengths of a shaft of a soft tissue anchor delivery device useful for treating a pelvic condition may be in a range from 10 to 22 centimeters, e.g., from 13 to 20 centimeters, especially for use in a female patient to laparoscopically or transvaginally access a posterior location of a pelvic region such as a region of sacral anatomy. Exemplary diameters of a shaft of a soft tissue anchor delivery device may be suitable to pass through a surgical incision, e.g., laparoscopically through a laparoscopic cannula or a laparoscopic trocar. Exemplary diameters can be in a range from ⅛ inch to I inch, e.g., from ⅛ inch to % inch, or from ⅛ inch to Yz inch. Other lengths and diameters may be useful for different uses of the device; a shorter shaft may be useful for working on tissue that is more easily accessed or closer to a surgical opening of a patient; larger diameters may be useful for applications that are not laparoscopic, or for applications that involve a soft tissue anchor of larger dimensions.

According to examples of described devices, the shaft, e.g., at a distal end or distal region of the length, can include a lengthwise magazine or equivalent space or holding area capable of containing one or more soft tissue anchor. The magazine or the device in general is also preferably capable of advancing one or a series of multiple connected or unconnected soft tissue anchors in a distal direction, e.g., from a proximal position along a length of the shaft to a more distal position along the length of the shaft. The magazine can be in communication with one or more additional spaces designated and useful to hold a soft tissue anchor, stage a soft tissue anchor, or eject a soft tissue anchor from a tip of the distal end and into soft tissue.

The handle, shaft, and shaft distal end, can also include one or more locations and mechanisms (e.g., internally) that can be controlled from the proximal end, to manipulate one or a series of soft tissue anchors in a magazine or other position in the shaft, to advance a soft tissue anchor distally or to eject a soft tissue anchor from a tip of the shaft. For example, the device (e.g., handle or shaft) may include an advancing mechanism that can be actuated from the proximal end to advance a soft tissue anchor (or series of anchors) in a distal direction within the magazine. The shaft may include a staging mechanism (that may be the same as or different from the advancing mechanism) that can be actuated from the proximal end to transfer a single soft tissue anchor from a position in the magazine to a staging position. The shaft may include an ejecting mechanism that can be actuated from the proximal end to eject a soft tissue anchor, or a portion thereof, from a tip of the shaft in a manner that can insert the soft tissue anchor (or a portion thereof) into soft tissue such as supportive tissue or supported tissue, such as through a sharpened hollow needle.

Figures included herewith show exemplary embodiments of soft tissue anchor delivery devices (sometimes merely "devices" for short, herein). FIG. 1A shows device 100 having proximal end 102, distal end 104, and shaft 110 extending therebetween. Handle 108 is located at proximal end 102 and includes actuator (e.g., trigger) 112. Distal end 104 (also a distal end of shaft 110) includes longitudinal (lengthwise) magazine 116 extending along a length of shaft 110. The device can allow manipulation of a soft tissue anchor by steps of advancing the anchor distally within the magazine, transferring a single anchor from the magazine to a staging location distal to the magazine, and ejecting the anchor from the staging location into tissue, e.g., through a sharpened hollow needle.

Still referring to FIG. 1A, magazine 116 can hold and maintain one or a series of soft tissue anchors (also: "fasteners" or "plastic fasteners") 114 longitudinally along a length of shaft 110. Magazine 116 may optionally be structured to contain each anchor 114 completely within shaft 110, and to engage both of legs 124, 125 within parallel magazine channels 136. An outer cover or cowling (e.g., cylindrical cover 111) can be present on an outer surface of shaft 110 to at least partially close the interior of shaft 110 and prevent any portion of anchors 114 (e.g., a leg 124, 125, or tie 126) from extending loosely away from shaft 110; this can prevent contact between tissue and a portion of an anchor during use of device 100.

Tip (or "distal end tip") 106 includes one or more aperture 120 capable of ejecting soft tissue anchor 114 or a portion thereof such as a leg (124, 125) from tip 106 and into tissue. Aperture 120 is a distal end of an opening that extends longitudinally along a length of shaft 110 in a proximal direction, and is defined by needle 115. Optionally and as illustrated, tip 106 can also include a sharpened needle end 122, which includes aperture 120 in the form of an internal channel 120 (extending into needle 115) through which a portion of soft tissue anchor 114 (e.g., such as leg 124, 125) can be passed, and from which the portion of soft tissue anchor 114 can be ejected to enter (and optionally pass through) tissue, with needle 115 being inserted into the tissue or through the tissue. Tip 106, as illustrated, includes two sharpened needle ends 122, each including aperture 120, and each of which can be placed through an implant material (of a first tissue) and then within tissue (not shown) (e.g., a first tissue or a second tissue), together. With each needle 115 placed in tissue, legs 124 and 125 of soft tissue anchor 114 can be passed through each of the two apertures 120, to be inserted into the tissue, while also being passed through material of an implant or a second tissue. A result can be as shown at FIG. 3A: an implant 127 (alternately tissue) held to tissue 129 by fastener 114, with two legs (124 and 125) being located below tissue 129 and tie 126 extending between the legs and also through implant 127 to hold implant 127 against tissue 129.

Referring again to FIGS. 1A, 1B, and 1C, device 100 includes proximal end handle 108, which contains mechanisms that allow for indexing, staging, and ejection of soft tissue anchor 114, leg 124, leg 125, or both legs 124 and 125 from tip 106. The mechanism can include, for example, a trigger and one or more pushrod (not shown) extending along shaft 110 through a length of needle 115, which can be moved distally to push a leg 124, 125, distally out of an aperture 120; a mechanism can optionally include two such pushrods, one each for independently ejecting leg 124 and leg 125 from respective apertures 120 of needles 115, simultaneously or separately. In use, needle or needles 115 can be placed through implant material (e.g., an extension portion of an implant) or a tissue, and also can be placed to penetrate tissue (e.g., a second tissue) at a surgical location; legs 124, 125 can be advanced along the length of shaft 110 to staging area 140 An actuator (e.g., trigger 112) at handle 108 can be moved to advance the one or more pushrods to move legs 124 and 125 distally through apertures 120, to eject legs 124 and 125 into tissue. In preferred devices, a single movement or "stroke" of trigger 112 can be sufficient to pass leg or legs 124, 125 from distal end 106 and into tissue.

Figure 1B:
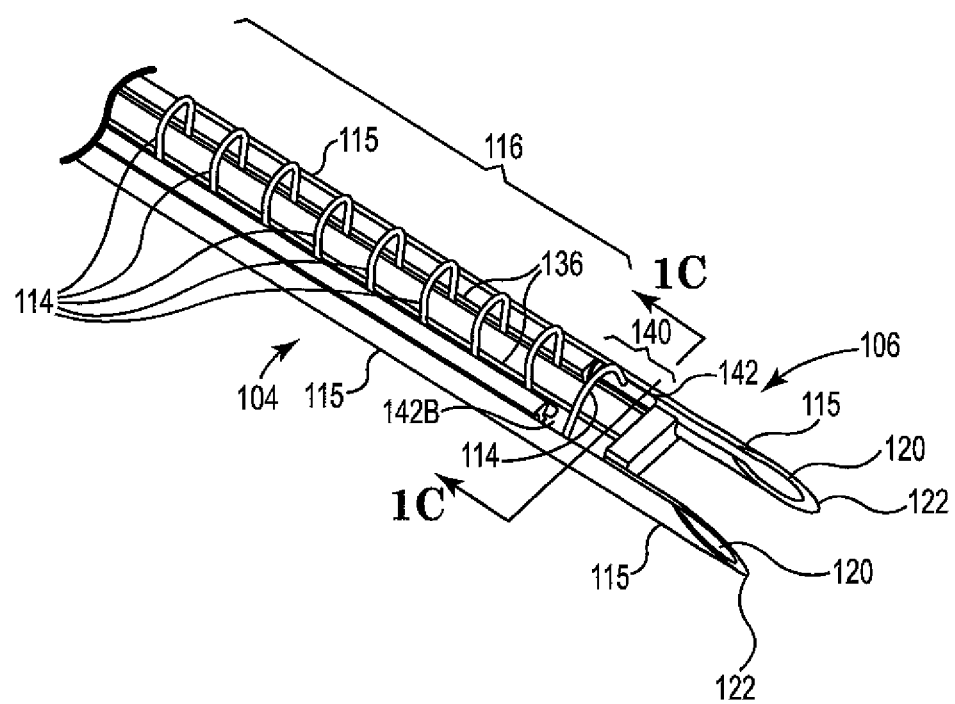

FIG. 1B is a more detailed illustration of distal end 104 of FIG. 1A. FIG. 1C is an end view of a cross section of shaft 110. As shown, magazine 116 of device 100 can support and hold a series of connected or unconnected "H"-type soft tissue anchors 114. Each soft tissue anchor 114 includes two legs 124, 125, situated in 15 parallel with lengths of legs 124, 125 extending parallel to a longitudinal axis and length of shaft 110. Legs 124, 125 of each soft tissue anchor 114 are connected by tie 126. Each leg 124, 125 of soft tissue anchor 114 can be considered to include a distal end 130 and a proximal end 132. Optionally, these distal and proximal ends 130 and 132 may be equivalent, e.g., in length and form.

Shaft 110 as illustrated includes two parallel magazine channels 136 running lengthwise along shaft 110 and in communication with or as part of magazine 116. As shown at FIG. 1B, each of legs 124, 125 can be inserted into one of parallel magazine channels 136. At rest, tie 126 of anchor 114 can optionally be biased to be straight or arched (e.g., bent) (see FIGS. 2B and 2A, respectively). A series of connected or unconnected anchors 114 can be placed into magazine 116 (see FIG. 1B) by loading each of the two legs 124, 125 into a proximal end opening (not shown) of the two parallel magazine channels 136. Each anchor or the series of anchors can be advance distally along a length of magazine 116 by an advancing mechanism (not shown) such as one or more pushrod within one or more of magazine channels 136. When legs 124, 125 are inserted into magazine channels 136, tie 126 is bent and optionally under strain while located within magazine 116. Specifically, ties 126 of anchors 114 are bowed when legs 124, 125 are held at magazine channels 136 (see FIGS. 1B and 1C).

Located at the distal end of magazine channels 136 is staging position 140, which includes two staging spaces 142a and 142b along a length of shaft 110, each in communication with one of magazine channels 136 and at a location distal to the ends of channels 136 but on a proximal side of sharpened ends 122 of needles 115. Measured laterally from a longitudinal axis or center of shaft 110, the location of each staging space 142a, 142b, is farther away from (farther "outboard" ot) the longitudinal axis of shaft 110, than are the locations of each of magazine channels 136; accordingly, the distance between each of staging spaces 142a and 142b is greater than the distance between the two magazine channels 136, as illustrated. Each staging space 142a, 142b, is sized to accept a leg 124 or 125 of an anchor 114, e.g., has a length that is at least equal and preferably slightly greater than a length of each of legs 124 and 125, and is aligned with an aperture 120 of a needle 115 to allow ejection from tip 106 in a distal direction.

In use, a magazine pushrod (not shown) in one or both of magazine channels 136, or another type of advancing mechanism at a location of shaft 110 or handle 108, can be actuated to move in a distal direction to engage a proximal end 132 of leg or legs 124, 125 of anchor 114, or a proximal end of a proximal anchor of a series of anchors 114 held in magazine channels 136, or a proximal end of a strip that includes a series of anchors 114. The magazine pushrod or the other advancing mechanism can be used to push an anchor 114 or series of anchors 114 in a distal direction. Upon being advance to and past a distal end of magazine channels 136 and magazine 116, legs 124, 125 of a distalmost anchor 114 are expelled from magazine channels 136 and are received into staging spaces 140a and 142b to rest within a needle channel of needles 115, the needle being aligned with apertures 120. Because the distance between each of staging spaces 142a and 142b is greater than the distance between the two magazine channels 136, legs 124 and 125 spring laterally into spaces 142a and 142b, as strain on tie 126 is partially released. See figure IB. See also FIG. 1C, which shows legs 124 and 125 located within channels 136 before being released into spaces 142a and 142b; the locations of spaces 142a and 142b are aligned with apertures 120 as illustrated at FIG. 1C.

In an ejection step, an ejection pushrod (not shown) located in one or both of needle channels of needles 115, e.g., extending along shaft 110 between handle 108 and distal end 104, can be moved distally to engage a proximal end 132 of one or both of legs 124, 125 located within staging spaces 142a, 142b. The ejection pushrod or pushrods can push one or both of legs 124, 125, through apertures 120 to eject legs 124, 125 out of sharpened needle ends 122 and into tissue, through implant material, or through implant material and into tissue, or through multiple tissues; the ejection causes two ends of tie 126 (each end connected to a leg 124, 125) to pass through both the tissue, implant material, etc., also causing a center length of tie 126 to remain external to the tissue and to engage and hold the implant material (or tissue) against the tissue (see FIG. 3A). In preferred devices, a single movement or . . . stroke" of trigger 112 can be sufficient to pass leg or legs 124, 125, from a location at a distal end of magazine channels 136, distally to become located at staging spaces 142a, 142b, and also to cause one or two ejection pushrods to move distally to then push leg or legs 124, 125 further distally to eject leg or legs 124, 125 from the ends of needles 115 and into tissue.

FIG. 3A shows an exemplary configuration of anchor 114 after ejection from device 100 of FIGS. 1A-1C, having two parallel needles 115. As shown, each of legs 124 and 125 have been ejected from distal end 106 of device 100, passed through implant material 127, and then into or optionally through tissue 129, to become secured by or within tissue 129. Each of two ends of tie 126 extend through tissue 129 and also through implant material 127, to secure implant material 127 to tissue 129. Tissue 129 may be any tissue, e.g., tissue of a pelvic region, such as a supportive tissue. Implant material 127 may be any implant material that is part of any type of implant, such as an extension portion of an implant. Implant material 127 as illustrated is designated to be an implant material, but this material may alternately represent a second tissue, attached by anchor 114 to the first tissue 129. In alternate embodiments, e.g., by use of different delivery devices, the tissue anchor may be situated differently relative to a tissue, an optional implant material, and an optional second tissue, for example as shown at FIG. 3B and at FIG. 6. As illustrated at FIG. 3B, implant 127 (alternately tissue) is held to tissue 129 by fastener 114, with two legs (124 and 125) being located above tissue 129 and implant (or tissue) 127, and tie 126 extending between the two legs and also through tissue 129 to hold implant 127 (alternately tissue) against tissue 129.

FIG. 4 shows another example of a soft tissue anchor delivery device 100, which includes certain features and structure that are similar to device 100 of FIG. 1A, specifically including proximal end 102, distal end 104, shaft 110 extending therebetween, handle 108, actuator (e.g., trigger) 112, and longitudinal (lengthwise) magazine 116 extending along a length of shaft 110. Device 100 of FIG. 4 differs from device 100 of FIG. 1A by way of various structural differences relating to magazine 116 and mechanisms for advancing, staging, and ejecting an anchor 114 from distal end 106.

In general terms, device 100 of FIG. 4 includes a long (e.g., extruded metal or plastic) shaft 110 containing magazine 116, which in turn can contain a collated strip of molded polymeric (plastic) fasteners 114. The device can allow manipulation of an anchor by steps of advancing the anchor distally within the magazine, transferring a single anchor from the magazine to a first staging location, transferring the single anchor from the first staging location to a second staging location (which is also referred to as the "ejecting location"), and ejecting the anchor from the second staging location, into tissue.

A rotating tip (or disc 160, which is capable of rotating about an axis aligned with or coinciding with a longitudinal axis of shaft 110) situated at the distal end of the magazine can accept a tissue fastener from the collated strip, and can rotate to shear the distal-most or terminal fastener 114 off of the strip; rotating tip (or disc 160), when rotated, aligns one leg (124) of that fastener 114 {the cross-section thereof) with aperture 120 of needle 115. Needle 115 is structurally built into an optional end cap (170) that covers rotating disc 160. (In alternate embodiments, a needle (e.g., 115) can be located at any other useful location, such as by being directly incorporated into rotating disc 160, in which case cap 170 may be eliminated.)

Figure 9:
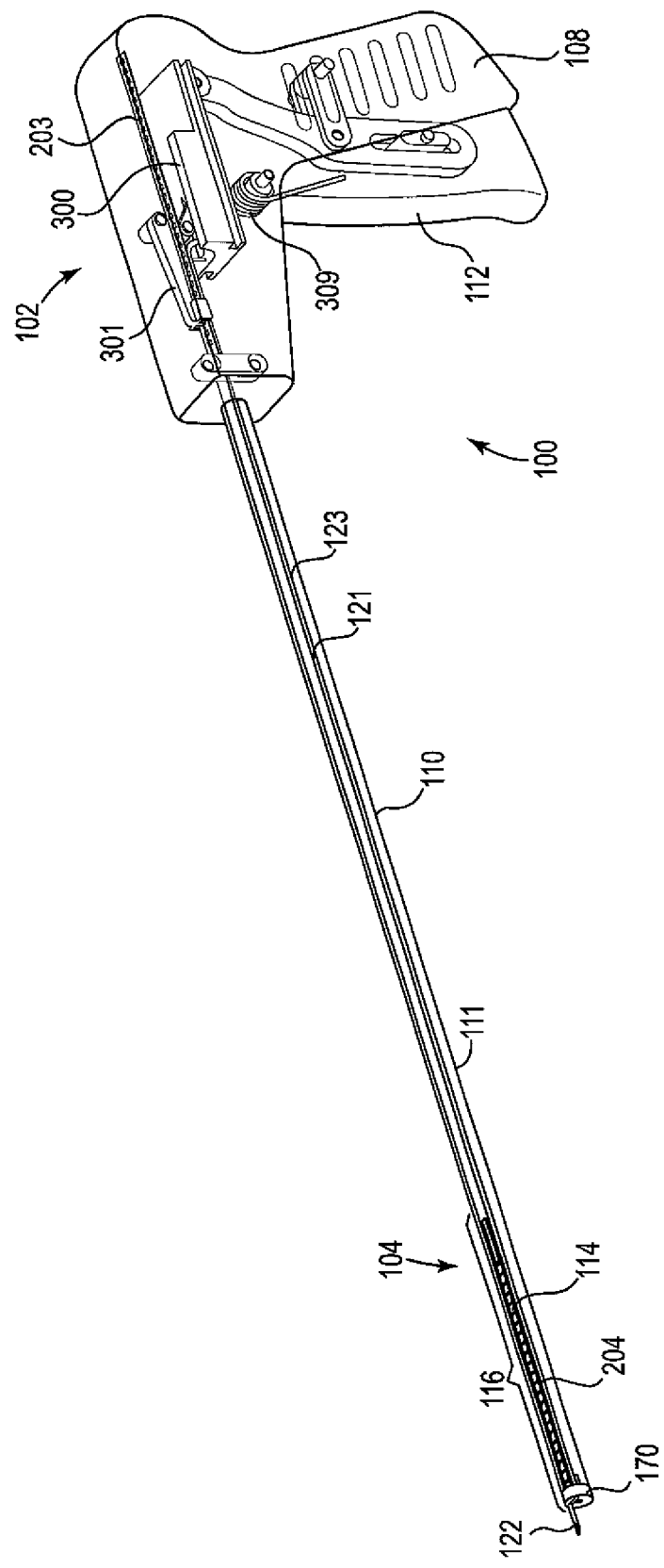
Figure 10:
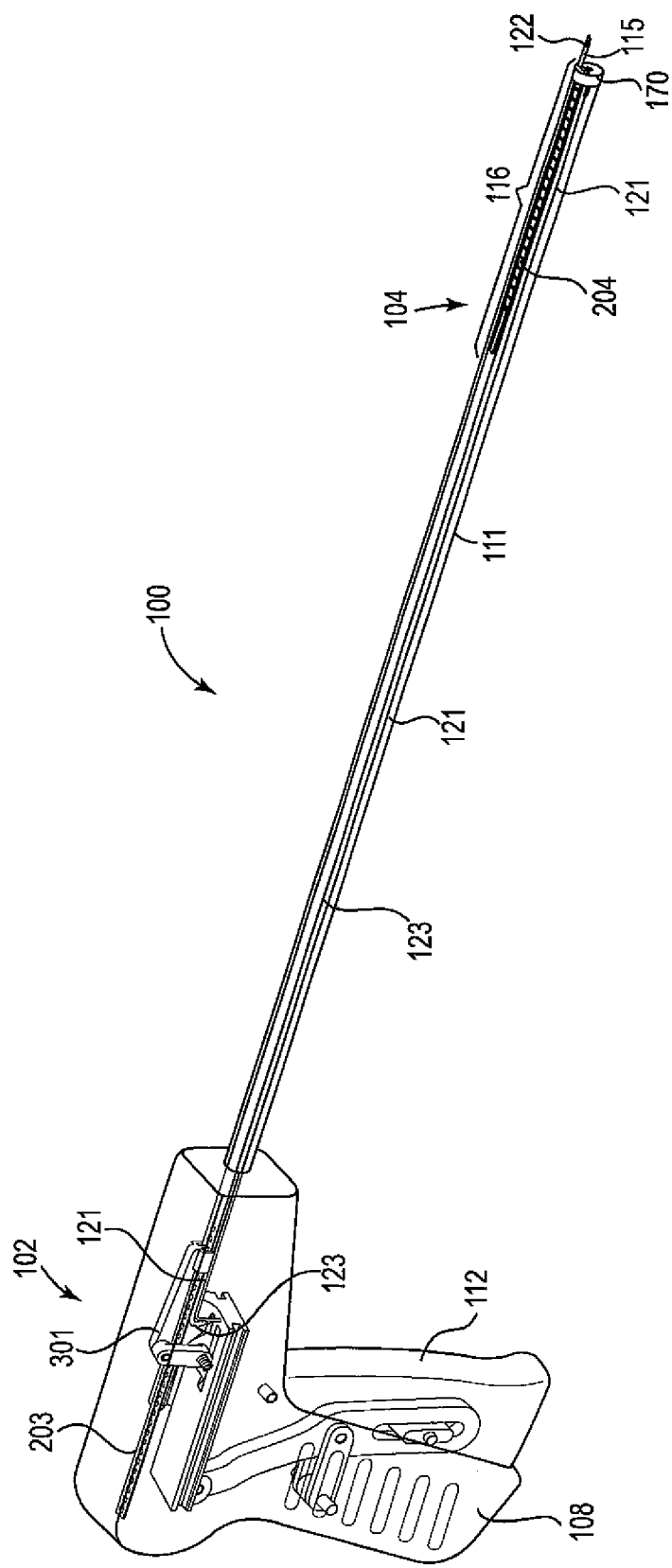

Rotating disc 160 is driven by a rotating staging shaft (123 at FIGS. 8C, 9, 10) extending along a length of shaft 110, e.g., from proximal end 102 to distal end 104, including along the length of magazine 116. A pin or molded feature 166 provides a stop to ensure correct alignment of rotating disc 160 at both limits of its rotation. Once in place, after rotation of rotating disc 160, a leg of the terminal fastener 114 can be ejected through aperture 120 of hollow needle 115 by a push rod (e.g., ejection push rod 121 at FIGS. 5C, 8C, 9, 10) also extending along the length of shaft 110, e.g., from proximal end 102 to distal end 104, including along a length of magazine 116. The actuation mechanism for causing rotation of rotating staging shaft 132, and distal movement of ejection pushrod 121, as well as an indexing mechanism for the collated strip, are located at proximal end 102, e.g., within handle 108, and can be operated by movement of trigger 112; preferably a single stroke of trigger 112 is effective to actuate all three of the indexing mechanism (to advance an anchor 114 along a length of shaft 110), the rotating staging shaft 123 (to stage a distal-most fastener 114), and the ejection pushrod (to eject a staged fastener 114 distally from sharpened tip 122 of needle 115).

Referring to FIGS. 5A, 5B, and 5C, features of device 100 of these figures that are similarly structured and numbered relative to FIG. 1A can perform generally similar functions. Referring to FIG. 5A, distal end 104 includes features that include shaft 110 and magazine 116. A series of fasteners 114 resides in magazine 116 with each of legs 124, 125 held in one of two parallel magazine channels 136 extending internally and longitudinally along a length of shaft 110; ties 126 extend laterally between legs 124, 125 and channels 136.

FIG. 5A shows distal end 104 exclusive of end cap 170 (which is optional) and needle 115 (which may alternately be located at rotating disc 160), to better illustrate features of rotating (staging) disc 160 with a fastener 114 loaded (staged) within disc 160; disc 160 is situated in a non-rotated position or a "staging" position. Fastener 114 is located within staging slot 162 of disc 160. FIG. 5B also shows distal end 104 exclusive of end cap 170 and needle 115; at FIG. 5B, disc 160 has been rotated (counterclockwise from the perspective of the viewer of FIG. 5B) into a deployment or "ejection" position. During rotation from the non-rotated staging position shown at FIG. 5A to the "ejection" position illustrated at FIG. 5B, terminal fastener 114 has been sheared off of the strip or series of (e.g., connected) fasteners 114 located and positioned end-to-end (of legs 124, 125) along a length of magazine 116; leg 124 has been rotated and is now aligned with a position of needle 115 (not shown). Legs 124 and 125, and tie 126, all are located within staging slot 162 of disc 160.

FIG. 5C shows distal end 104 including optional cap 170, and shows rotating disc 160 in the ejection position also illustrated at FIG. 5B. End cap 170 is stationary at the end of shaft 110. Needle 115 of stationary end cap 170 is aligned with ejection push rod 121 extending along shaft 110; curved slot 172 of end cap 170 aligns with curved slot 162 of rotating (staging) disc 160 when disc 160 is rotated to 30 the "ejection" position of FIG. 5B.

Different from distal end I 04 of device 100 of figure IA, distal end 104 of FIGS. 5A, 5B, and 5C includes a staging mechanism in the form of rotating (staging) disc 160. As anchors 114 are advanced distally within magazine 114 (by any form of advancing mechanism), a distal-most anchor 114 becomes located within curved slot 162 of rotating (staging) disc 160. In specific, legs 124, 125 of anchors 114 are contained at two ends of curved slot 162, with distal ends 130 of legs 124, 125 passing first into slot 162. Tie 126 is also within slot 162. The lengthwise dimension (along the longitudinal axis of shaft 110) of disc 160 and slot 162 is about the same dimension as the lengthwise dimension (along the longitudinal axis of shaft 110) of each of legs 124, 125.

Referring to FIG. 5C, shown in this figure and not in FIGS. 5A and 5B is optional end cap 170 at tip 106. Tip 106 (including optional end cap 170) includes a single longitudinal channel or aperture 120 capable of ejecting a single leg 124 of soft tissue anchor 114 into tissue. Aperture 120 extends through needle 115 and sharpened needle end 122, which extends in a proximal direction and is in communication with channel 119 extending longitudinally along a length of shaft 110. Channel 119 also includes ejection pushrod 121, which can be actuated to move distally to push leg 124 and eject leg 124 through aperture 120 of needle 115. Optional end cap 170 includes curved slot 172, which aligns with slot 162 of disc 160, with disc 160 in the deployment (ejection) position (also considered a "second staging position"). Slot 172 is stationary and is sized to allow passage of anchor 114.

Device 100, e.g., at handle 108 or shaft 110, also includes a staging mechanism including staging shaft 123 that connects to rotating (staging) disc 160, to rotate disc 160 between a non-deployed position (staging position, shown at FIG. 5A) and a deployed position (ejection position, or second stating position, shown at FIG. 5B). As shown at FIG. 5A, with legs 124, 125 and tie 126 of anchor 114 contained in slot 162, disc 160 can be rotated. Rotation of disc 160 moves anchor 114 contained in slot 162 rotationally, to a second staging position for ejection. Optionally and preferably, multiple anchors 114 of a series of anchors in magazine 116 are connected at ends of legs 124, 125 (a distal end of a proximal anchor 114 is connected to a proximal end of an adjacent anchor 114). Rotation of disc 160 will also break off the distal-most anchor 114 from the series, i.e., the anchor held within slot 162, from the adjacent, next proximal anchor. With anchor 114 staged in the second staging position (within slot 162 of rotated disc 160 in its deployed or "ejection" position) as shown at FIGS. 5B and 5C, ejection pushrod 121 can be moved distally to contact a proximal end 132 of the leg 124, 125 of anchor 114 that is aligned with channel 119 and aperture 120 of sharpened needle 115. Ejection pushrod 121 can be advanced distally to push first leg 124 (leading leg or ejected leg) through aperture 120 and into tissue; the rest of anchor 114, i.e. tie 126 and second (following) leg 125, passes through slot 172 of end cap 170, optionally through an implant, and into tissue. Ejected leg 124 enters tissue; tie 126 extends from ejected leg 124 to a location external to the tissue and can optionally pass through an implant material or another tissue; the second leg 125 is located on a proximal side of the optional implant material or second tissue, on a side of the opposite of the first tissue, and the implant material or tissue through which tie 126 passes is secured to the tissue by second leg 125 (see, e.g., FIG. 6).

Referring to device 100 of FIGS. 4 and 5A, 5B, and 5C, in use, anchors 114 are loaded into magazine 116. An advancing mechanism advances an anchor 114 or a distal-most anchor 114 through magazine 116 and into slot 162. Disc 160 is rotated by actuation of and rotation of staging shaft or cam 123 (see FIGS. 5C and SC), causing rotating disc 160 to rotate from a non-deployed (staging or first) position (FIG. 5A) to a deployed position (or second staging position, FIG. 5B) in which anchor 114 located in slot 162 is in an ejection position. Subsequently, ejecting pushrod 121 can be actuated and moved distally to contact a proximal end 132 of a first leg 124 of anchor 114, located in slot 162 and aligned with aperture 120 of sharpened needle 115. Sharpened needle 115 can be passed through an implant material and tissue, or tissue and tissue. Ejection pushrod 119 then is advanced distally to push first leg 124 through aperture 120 of sharpened needle 122, through the implant material and into the tissue, optional implant, etc. Tie 126 and a second leg 125 of anchor 114 is carried out of slot 162, passes through slot 172, and holds tissue or implant material against the tissue.

FIG. 6 shows an example of anchor 114 after ejection from device 100 of FIGS. 4 and 5A, 5B, and 5C, having a single needle 115 for ejecting a single leg of anchor 114 into tissue. As shown, one leg (124) (the "first" leg, or an "ejected" leg) has been passed through tissue 129 to become secured within tissue 129. Tie 126 extends through tissue 129 and implant material 127, and the second leg (125) holds implant material 127 against tissue 129. Implant material 127 as illustrated is designated to be an implant material, but this material (127) may alternately represent a second tissue attached by anchor 114 to the first tissue 129.

Figure 7C:
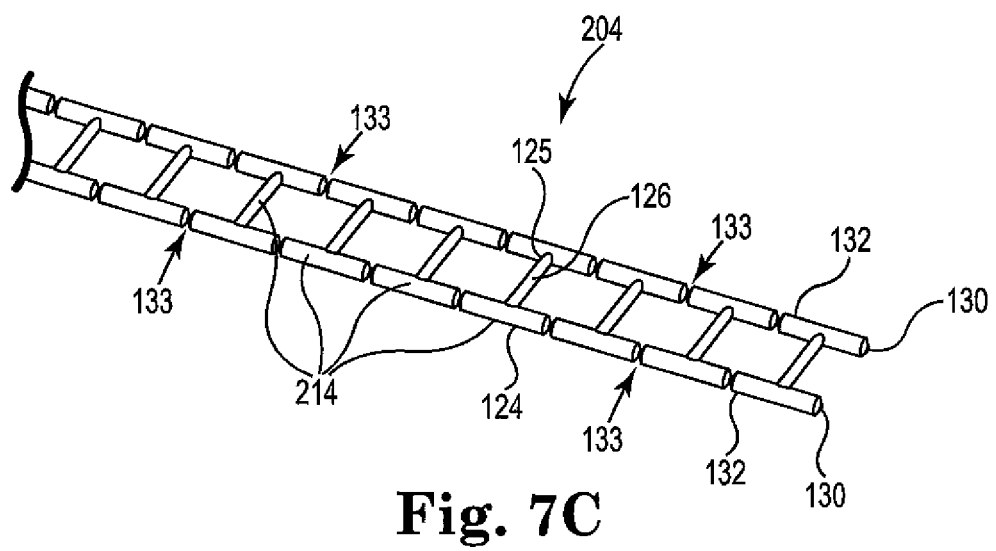
Figure 7D:
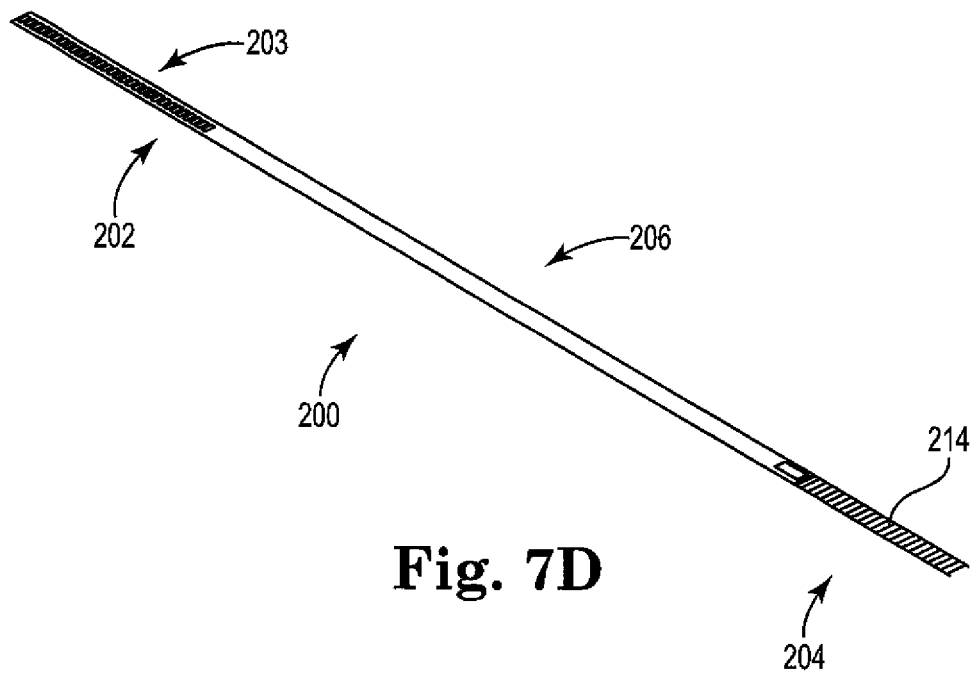

FIG. 7 A through 7D show examples of fastener strips ("soft tissue anchor strips") 200 that include proximal end 202, distal end 204, and mid portion 206. Proximal end 202 and mid portion 206 can be made of any useful material, such as metal or plastic and in use in device 100 can reside in a longitudinal lumen sized and shaped to receive these portions of strip 200. Proximal end 202 includes an indexing feature for engaging an indexing (or "advancing") mechanism of a device 100; the indexing feature (203) may include a set of apertures (e.g., rectangular, square, round, oval, etc.), a set of teeth, or another regularly-repeating surface or structure useful for moving strip 200 distally a regular distance equal to a length of legs 124, 125 of a fastener 114, with each single actuation (stroke or throw) of an actuating mechanism at proximal end 102, such as trigger 112. Distal end 204 includes a series of soft tissue anchors 114. Each anchor 114 is connected to one or two adjacent anchor or anchors in the series, with proximal ends 132 of legs 124, 125 of each anchor 114 being connected to distal ends 130 of legs 124, 125 of an adjacent (more proximal) anchor in the series. The connections 133 between the proximal ends and the distal ends of the adjacent anchors 114 are joints, e.g., frangible joints, or a frangible hinge, that can be made of the same material as fasteners 114, but of reduced size (e.g., diameter and cross section). Connections 133 can be broken (e.g., sheared or pulled apart) by a mechanism at a distal end of a shaft 110 of a device 100, such as by an advancing mechanism, by a staging mechanism (e.g., by rotation of disc 106 while a terminal tissue fastener 114 is located in slot 162), or by another mechanism.

Figure 8A:
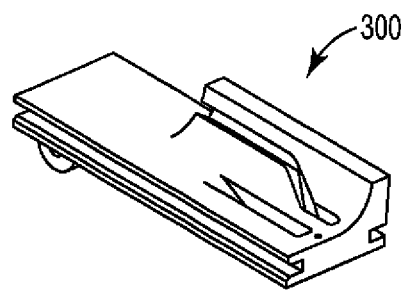
FIGS. 8A, 8B, 8C, 9, and 10 show an exemplary delivery device.
Figure 8B:
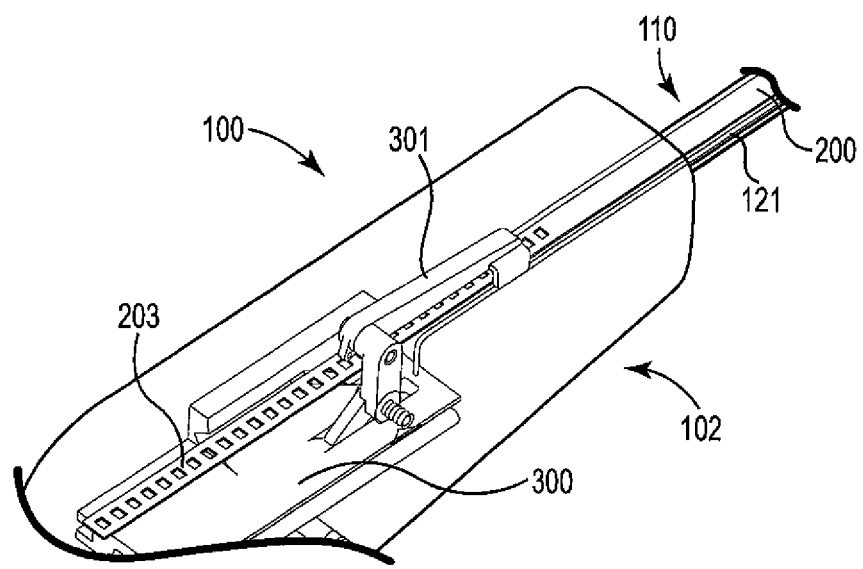
Figure 8C:
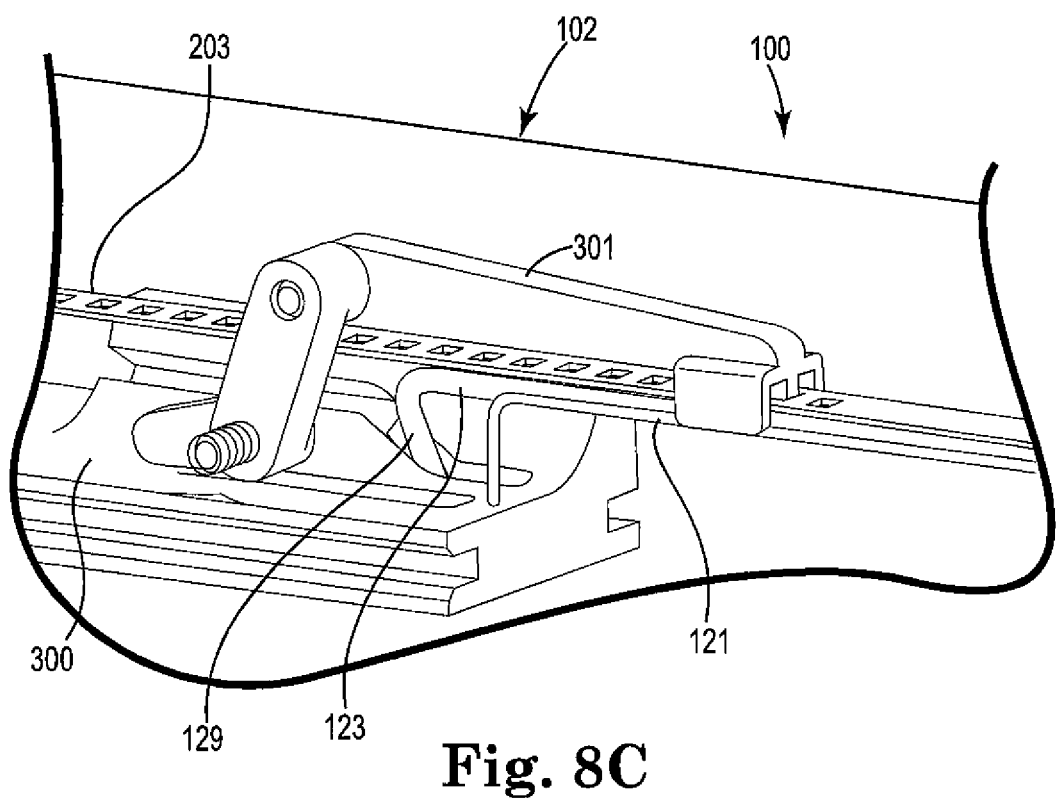

FIGS. 8A, 8B, and 8C, show certain details of an exemplary actuating mechanisms and related structure in a device 100 (of FIG. 4), capable of advancing a soft tissue anchor 114, staging the soft tissue anchor 114, and ejecting the soft tissue anchor 114 from a distal end of shaft 110 of device 100; preferred mechanisms allow for all three of advancing, staging, and ejecting the soft tissue anchor 114 to occur by a single pull of an actuator such as a trigger (112), lever, or other actuating mechanism.

According to the illustrated embodiment of device 100 and the details of its actuating mechanisms, a delivery and indexing cycle can include four steps or phases: 1—A step to advance fastener strip 200 one unit to move a terminal fastener 114 into slot 162 of rotating tip 160; 2—A step of rotating disc 160 about a longitudinal axis of disc 160 and shaft 110, to shear a terminal fastener (114) off of a distal end of distal portion 204 of strip 200, and align one leg (124) of the terminal fastener 114 with aperture 120 and push rod 121; 3—A step of ejecting the terminal fastener 114 through and out hollow needle 114, but distally pushing push rod 121; and 4—A reset step. These operations are all driven by cams on a carriage driven through linkages in the handle, or any other suitable mechanism or combination of mechanisms.

Referring to FIGS. 8A, 8B, and 8C, when trigger or lever 112 is squeezed or moved, an inclined plane on carriage 130 causes rocker 301 to rotate forward, and through a pawl, advances index strip 203 of strip 200 precisely the length of one fastener leg (124, 125). This moves the last fastener 114 on strip 200 into slot 162 of rotating tip 160 at the end of shaft 110 (i.e., into a first staging position). During this phase, cam follower 129 on the rotating staging shaft 123 is in a straight segment of the cam profile of carriage 300, so that staging shaft 123 is not caused to rotate.

After the terminal fastener 114 is advanced into rotating tip 106, cam follower 129 on rotating staging shaft 123 enters the helical portion of the cam profile of carriage 300, causing staging shaft 123 to rotate, which causes disc 106 to rotate and shear the terminal fastener 114 off of the distal end of strip 202; fastener 114 has been rotated into an ejecting position (a second staging position) with one leg (124) of fastener 114 aligned longitudinally with aperture 120 of needle 115 and also with push rod 121.

Referring to FIG. 8C, after rotation of disc 160 through a desired angle, the cam profile becomes straight again so rotating disc 160 does not rotate further. Carriage 300 continues to move forward (distally). Push rod 121 pushes the leg 124 of fastener 114 through and out the hollow needle 115 for ejection, e.g., into tissue.

After ejection of leg 124, spring 309 causes carriage 300 to return to its initial position. Rocker 301 rotates back as it goes back to the bottom of the inclined plane and resets the pawl.

According to exemplary uses of certain described soft tissue anchor delivery devices and related systems, including implants, a transvaginal method to reach a sacral promontory can include:

1—Complete an incision at a desired location for a desired technique; e.g., through the vaginal apex (or posterior to the apex) and the peritoneum for a transvaginal method, or at one or multiple abdominal locations for a laparoscopic method 2—Introduce an implant or implant material through the incision (e.g., through a laparoscopic trocar or cannula);

3—Confirm sacral promontory (bone=firm feel, promontory=increased depth with minimal anterior movement) (e.g., laparoscopically);

4. —Using a soft tissue anchor delivery device (e.g., 100) as described, secure the implant or implant material to tissue of the sacral promontory by placing a fastener through the implant or implant material and into tissue of the sacral promontory (e.g., as indicated at FIG. 3 or 6) (e.g., laparoscopically);

5. —Remove the soft tissue anchor delivery device.

When the procedure is performed using an abdominal incision such as an open abdomen incision, or when the procedure is performed laparoscopically, instead of a vaginal incision (transvaginally) as specified, the steps can be similar except that step 1 above is to complete an incision through an abdomen (either an open incision or a laparoscopic incision) and not a vagina.

Soft tissue anchor delivery devices as described and illustrated can be used and useful by a method of inserting the device into a surgical incision, for example a transvaginal, laparoscopic, or abdominal incision, and manipulating the distal end and distal end tip to a desired surgical location, such as a location of soft supportive tissue. For performing an SCP or other procedure, a shaft of the soft tissue anchor delivery device can be passed through an incision to place the shaft distal end at a region of sacral anatomy. The soft tissue anchor delivery device can be used to secure a portion of a pelvic implant to tissue at the region of sacral anatomy, such as to an anterior longitudinal ligament. The method can optionally also involve a tool (e.g., retractor or expansion member), implant, adjustable implant, anchor, or other device or method, e.g., as described at Applicant's co-pending International Patent Application having International Patent Application number PCTJUS2010/062577, filed Dec. 30, 2010, published as WO 2011/082350, the entirety of which is incorporated by reference.

For other treatment methods, such as hernia repair, the distal end of a soft tissue anchor delivery device can be placed at a different anatomical location, depending on the type of repair. Described anchors and tools as described can be useful for still other treatments and procedures, such as general surgery procedures, veterinary procedures for treating animals, and plastic surgery for treating muscle or skin tissues such as at a face, leg, stomach, or abdomen.

A soft tissue anchor delivery device as described and its components can be made from any suitable material or combination of materials. Examples include materials that are known to be useful with surgical devices and tools, including stainless steel, nitinol, polycarbonate, polypropylene, polyethylene, fluoropolymer, PET, polyurethane, silicone, polysulphone, and ultem.

Implants, their various components, structures, features, materials and methods may have a number of suitable configurations as shown and described in the previously-incorporated references, or as described herein. Various methods and tools for introducing, deploying, anchoring and manipulating implants to treat prolapse or another pelvic conditions, as disclosed in the previously-incorporated references, are envisioned for use with the present invention as well as those methods and tools identified and described herein.

Also according to embodiments of the methods, implants, tools, and devices described herein, any of the described tissue anchors or insertion tools can be used for connecting one anatomical tissue (e.g., skin, muscle, or another soft tissue or organ tissue) to a second anatomical tissue, e.g., in a male or a female patient, or for veterinary use, and for any of a large variety of conditions, such as a pelvic condition, non-pelvic condition, or for a general surgical or specialty (e.g., plastic surgery) procedure.

Also according to embodiments of the methods, implants, tools, and devices described herein, any of the described tissue anchors or insertion tools can be used for placing any desired pelvic implant in a male or a female patient, or for veterinary use, and for any of a large variety of conditions, such as a pelvic condition, non-pelvic condition, or for a general surgical or specialty (e.g., plastic surgery) procedure. The implant can include any structural features useful for such treatment, including any desired size, shape, and optional features such as adjustability and anchoring systems. Any of these features may be previously known, future developed, described herein, or described in documents incorporated herein, for any particular implant and method. For example, the present description relates generally to anchors that can be useful for placing a surgical implant. An implant that is secured by any of the anchors described can be useful to treat a pelvic condition in a male or a female patient; as a single and non-limiting example, an implant that includes or uses an anchor as described can be used in a transvaginal or transabdominal SCP procedure to provide support to a vaginal cuff (apex), through an implant that is secured to tissue by the anchor, the anchor being attached at a region of sacral anatomy such as a sacral ligament (e.g., anterior longitudinal ligament, a.k.a. the "anterior ligament" or "longitudinal ligament").

The various systems, apparatus, and methods detailed herein are envisioned for use with certain known pelvic implants, repair systems (e.g., for male and female), and method steps, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, and U.S. Patent Publication Nos. 2002/151762, 2010/0174134, 2010/0298630, and 2002/147382. Accordingly, the above-identified disclosures are fully incorporated herein by reference in their entirety.

The presently described systems, their various components, structures, features, materials, and methods may have a number of suitable configurations as shown and described in the previously-incorporated references. Various methods and tools for introducing, deploying, and manipulating device, implants, anchors, and the like as disclosed in the previously-incorporated references are envisioned for use with the present invention as well. Various devices and methods described herein may advantageously facilitate reduction of total procedural time needed to treat a pelvic condition.

All patents, patent applications, and publications cited herein are hereby incorporated by reference in their entirety as if individually incorporated, and include those references incorporated within the identified patents, patent applications and publications.

What is claimed is:

1. A soft tissue anchor delivery device in combination with a soft tissue anchor,
the soft tissue anchor comprising a first elongate leg, a second elongate leg, and a tie connecting the first elongate leg to the second elongate leg, the soft tissue anchor being formed of a flexible material such that the anchor does not become permanently deformed when ejected by the soft tissue anchor delivery device,
the delivery device comprising
a proximal end and a distal end, the proximal end including a handle,
a shaft extending from the handle to the distal end, the distal end including
a magazine,
a staging location on a distal side of the magazine, and
a rotatable disc at the distal end of the delivery device, the rotatable disc includes a slot, the rotatable disc being configured to rotate about an axis of the shaft between a first position and a second position, and
an ejector that can be actuated to eject the anchor from the staging location.

2. The device and anchor of claim 1, wherein the first elongate leg has a length in a range from about 0.1 to about 1 inch, the second elongate leg has a length in a range from about 0.1 to about 1 inch, and the tie has a length in a range from about 0.1 to about 1 inch.

3. The device and anchor of claim 1, wherein the anchor is formed of a flexible plastic.

4. The device and anchor of claim 1, wherein the distal end of the delivery device is placed through a laparoscopic cannula to be located at a region of supportive tissue.

5. The device and anchor of claim 1, wherein the magazine is capable of holding a series of anchors located in a longitudinal alignment, the series including a distal anchor and a proximal anchor, with a proximal location of the distal anchor being connected to a distal location of the proximal anchor.

6. The device and anchor of claim 1, wherein the magazine is capable of holding a series of anchors located in a longitudinal alignment, the series including
a distal anchor having a first elongate leg and a second elongate leg connected by an elongate tie, each elongate leg having a distal end and a proximal end,
a proximal anchor having a first elongate leg and a second elongate leg connected by an elongate tie, each elongate leg having a distal end and a proximal end, with a proximal end of each elongate leg of the distal anchor being joined to a distal end of each elongate leg of the proximal anchor.

7. The device and anchor of claim 1, wherein the tie comprises a first tie end connected to the first elongate leg at a medial location, and a second tie end connected to the second elongate leg at a medial location of the second elongate leg.

8. The device and anchor of claim 7, wherein the magazine comprises a first magazine channel extending along a length of the distal end and a second magazine channel extending along a length of the distal end parallel to the first magazine channel, wherein the anchor can be held in the magazine with the first elongate leg located in the first magazine channel and the second elongate leg located in the second magazine channel.

9. The device and anchor of claim 7, wherein the distal end of the delivery device comprises
a hollow sharpened needle distal to the rotatable disc and extending parallel to the axis of the shaft, wherein
in the first position, the slot aligns with the anchor held in the magazine,
in the second position, one of the first elongate leg or the second elongate leg of the anchor aligns with the hollow needle.

10. The device and anchor of claim 1, wherein the rotatable disc includes a first slot and a second slot.

11. The device and anchor of claim 1, wherein the slot is a curved slot.

12. A soft tissue anchor delivery device in combination with a soft tissue anchor,
the soft tissue anchor comprising a first elongate leg, a second elongate leg, and a tie connecting the first elongate leg to the second elongate leg, the tie includes a first tie end connected to the first elongate leg at a medial location of the first elongate leg, and a second tie end connected to the second elongate leg at a medial location of the second elongate leg,
the delivery device comprising
a proximal end and a distal end, the proximal end including a handle,
a shaft extending from the handle to the distal end, the distal end including
a magazine,
a staging location on a distal side of the magazine, and
a rotatable disc at the distal end of the delivery device, the rotatable disc includes a slot, the rotatable disc being configured to rotate about an axis of the shaft between a first position and a second position, and
an ejector that can be actuated to eject the anchor from the staging location.

13. The device and anchor of claim 12, wherein the first elongate leg has a length in a range from about 0.1 to about 1 inch, the second elongate leg has a length in a range from about 0.1 to about 1 inch, and the tie has a length in a range from about 0.1 to about 1 inch.

14. The device and anchor of claim 12, wherein the anchor is formed of a flexible plastic and the anchor does not become permanently deformed when ejected by the soft tissue anchor delivery device.

15. The device and anchor of claim 12, wherein the distal end of the delivery device is placed through a laparoscopic cannula to be located at a region of supportive tissue.

16. The device and anchor of claim 12, wherein the magazine is capable of holding a series of anchors located in a longitudinal alignment, the series including a distal anchor and a proximal anchor, with a proximal location of the distal anchor being connected to a distal location of the proximal anchor.

17. A soft tissue anchor delivery device in combination with a soft tissue anchor,
the soft tissue anchor comprising a first elongate leg, a second elongate leg, and a tie connecting the first elongate leg to the second elongate leg,
the delivery device comprising
a proximal end and a distal end, the proximal end including a handle, a shaft extending from the handle to the distal end, the distal end including
a magazine,
a staging location on a distal side of the magazine, and
a rotatable disc at the distal end of the delivery device, the rotatable disc includes a curved slot, the rotatable disc being configured to rotate about an axis of the shaft between a first position and a second position, and
an ejector that can be actuated to eject the anchor from the staging location.

18. The device and anchor of claim 17, wherein the anchor is formed of a flexible plastic and the anchor does not become permanently deformed when ejected by the soft tissue anchor delivery device.

19. The device and anchor of claim 17, wherein the distal end of the delivery device is placed through a laparoscopic cannula to be located at a region of supportive tissue.

20. The device and anchor of claim 17, wherein the magazine is capable of holding a series of anchors located in a longitudinal alignment, the series including a distal anchor and a proximal anchor, with a proximal location of the distal anchor being connected to a distal location of the proximal anchor.

* * * * *